US011234908B2

(12) United States Patent
Quan et al.

(10) Patent No.: US 11,234,908 B2
(45) Date of Patent: Feb. 1, 2022

(54) NANOEMULSIONS COMPRISING SULFOALKYL ESTER AND/OR AMIDE OF FATTY ACIDS IN AQUEOUS PHASE

(71) Applicant: Conopco, Inc., Englewood Cliffs, NJ (US)

(72) Inventors: Congling Quan, Woodbridge, CT (US); David John Lang, Southbury, CT (US); Bruce Davis Casbarro, Hamden, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 85 days.

(21) Appl. No.: 16/499,984

(22) PCT Filed: Mar. 29, 2018

(86) PCT No.: PCT/EP2018/058097
§ 371 (c)(1),
(2) Date: Oct. 1, 2019

(87) PCT Pub. No.: WO2018/192761
PCT Pub. Date: Oct. 25, 2018

(65) Prior Publication Data
US 2021/0128421 A1 May 6, 2021

(30) Foreign Application Priority Data
Apr. 20, 2017 (EP) .................................... 17167394

(51) Int. Cl.
*A61K 8/06* (2006.01)
*A61K 8/31* (2006.01)
*A61K 8/46* (2006.01)
*A61K 8/92* (2006.01)
*A61Q 19/10* (2006.01)
*B82Y 5/00* (2011.01)

(52) U.S. Cl.
CPC ................. *A61K 8/062* (2013.01); *A61K 8/31* (2013.01); *A61K 8/466* (2013.01); *A61K 8/922* (2013.01); *A61Q 19/10* (2013.01); *A61K 2800/10* (2013.01); *A61K 2800/21* (2013.01); *B82Y 5/00* (2013.01)

(58) Field of Classification Search
CPC .......... A61K 8/062; A61K 8/31; A61K 8/922; A61K 8/466; A61K 2800/21; A61K 2800/10; A61Q 19/10; B82Y 5/00
See application file for complete search history.

(56) References Cited

U.S. PATENT DOCUMENTS

| 5,500,152 | A | 3/1996 | Helliwell |
| 5,584,293 | A | 12/1996 | Darrow et al. |
| 6,066,608 | A | 5/2000 | Glenn, Jr. |
| 6,541,018 | B1 | 4/2003 | Simonnet et al. |
| 8,772,212 | B2 | 7/2014 | Restrepo et al. |
| 8,834,903 | B2 | 9/2014 | Simonnet et al. |
| 2003/0012759 | A1 | 1/2003 | Bowen-Leaver et al. |
| 2003/0077299 | A1 | 4/2003 | Iwai et al. |
| 2008/0153729 | A1 | 6/2008 | Tsaur et al. |
| 2009/0062177 | A1 | 3/2009 | Tsaur |
| 2009/0062406 | A1 | 3/2009 | Loeffler |
| 2017/0087064 | A1 | 3/2017 | Ikeda et al. |

FOREIGN PATENT DOCUMENTS

| JP | H10259114 | 9/1998 |
| WO | WO02080864 | 10/2002 |

OTHER PUBLICATIONS

James Ziming Sun, et al.; Solubilization of sodium cocoyl isethionate; Journal Cosmetic Science Nov./Dec. 2003; pp. 559-568; vol. 54; Journal Cosmetic Science.
Search Report and Written Opinion in PCTEP2018058097.
Search Report and Written Opinion in EP17167394; dated Aug. 11, 2017.
IPRP1in PCTEP2018058097; Oct. 22, 2019; World Intellectual Property Org. (WIPO).
Warner M. Linfield; Anionic Surfactants Part II; Surfactant Science Series; Jan. 1, 1976; pp. 458-461 vol 7.

*Primary Examiner* — Robert S Cabral
(74) *Attorney, Agent, or Firm* — Krista A. Kostiew

(57) ABSTRACT

The present invention relates to novel oil-in-water pumpable nanoemulsions. The oil phase contains oil selected from the group consisting of triglyceride oil and/or petrolatum as well as $C_8$ to $C_{18}$ fatty acid; and the aqueous phase contains sulfoalkyl ester and/or amide of fatty acids as emulsifier.

14 Claims, No Drawings

NANOEMULSIONS COMPRISING SULFOALKYL ESTER AND/OR AMIDE OF FATTY ACIDS IN AQUEOUS PHASE

CROSS REFERENCE TO RELATED APPLICATIONS

The present application is a U.S. National Phase Application under 35 U.S.C. § 371 of International Application No. PCT/EP2018/058097, filed on Mar. 29, 2018, which claims priority to European Patent Application No. 17167394.0, filed on Apr. 20, 2017, the contents of which are incorporated herein in their entireties.

FIELD OF THE INVENTION

The present invention relates to novel oil-in-water (o/w) nanoemulsions. The nanoemulsions contain (1) an internal oil phase having triglyceride oils and/or petrolatum and $C_8$ to $C_{18}$ fatty acid; and (2) an external aqueous phase containing anionic surfactants which are sulfoalkyl ester and/or amide of fatty acids.

BACKGROUND OF THE INVENTION

The invention is concerned with the provision of nanoemulsions comprising triglyceride oils and petrolatum (benefit agents delivered from nanoemulsion) in small droplets (e.g., 400 nanometers or less); these are considered more aesthetically pleasing than compositions in which benefit agents are delivered in the form of larger oil droplets. The nanoemulsions further provides high deposition of the triglyceride oil and/or petrolatum when being incorporated in personal cleansing compositions. Further, surprisingly, excellent lather performance of personal cleansing compositions is found when these benefit agents are present in the form of droplets of 400 nanometers or less. Typically, the triglyceride oil and petrolatum benefit agents tend to depress lather speed and volume when in the form of droplets of a few microns.

Applicants have previously filed applications in which the primary emulsifiers (in aqueous phase) are N-acyl derivatives of mono- or di-carboxylic amino acids. Both of these can be supplied in the format of liquid solution with concentration ranging from 20 to 35% at ambient temperature. N-acyl derivatives of both dicarboxylic and monocarboxylic amino acid surfactants are exceptionally mild and quite expensive.

Sulfoalkyl ester and/or amide of fatty acids are other types of mild surfactants which are generally more economically produced than more expensive surfactants (e.g., the N-acyl derivatives of mono- or di-carboxylic amino acids noted above). One example of sulfoalkyl ester of fatty acids, sodium acyl isethionate, is a well-known mild anionic surfactant with widespread applications in cosmetic compositions, for example, Dove® Bath Bars, in which sodium acyl isethionate is the most abundant ingredient. Sodium acyl isethionate has also been formulated into liquid cleansers, such as bodywashes, to replace harsh surfactants, e.g. sodium laureth sulfate. The most widely used sulfoalkyl amide of fatty acids, sodium methyl alkyl taurates, are desirably mild and provide excellent foam, Producing nanoemulsions using sulfoalkyl ester and/or amide of fatty acids as a primary emulsifier in aqueous phase is functionally and economically appealing, however, very challenging. Oil droplets of nanoemulsions made with sodium acyl isethionate as only emulsifier tend to be larger, e.g., greater than 400 nanometer (nm) after one pass through a high pressure homogenizer at 5000 pounds per square inch (psi) pressure. Further, nanoemulsions made with sodium acyl isethionate tend to solidify at ambient temperature and are thus difficult to pump due to poor solubility of sodium acyl isethionate in water. Sodium cocoyl isethionate has a solubility of only 0.01% by weight in water at 25 C (J. Cosmet. Sci., 54, 559-568 November/December 2003).

The solubility of sodium methyl cocoyl taurate in water is around 1% by weight at 25 C. It can be supplied as a paste with 20 to 35% active. When using sodium methyl acyl taurate as the only emulsifier to prepare a nanoemulsion of petroleum jelly, though no solidification takes place at ambient temperature, the oil droplets are greater than 600 nm after one pass through a high pressure homogenizer at a pressure of 5000 psi.

Applicants have now found that use of fatty acid (in oil phase of nanoemulsion) as co-emulsifier provides several unexpected advantages. First, it permits the use of less expensive, poorly soluble anionic mild surfactants (e.g., sodium acyl isethionate) in preparation of pumpable nanoemulsions at ambient temperature. Also nanoemulsions of much smaller droplet size can be prepared more efficiently (e.g., lower process pressure and/or fewer passes through a homogenizer). Further, using fatty acid co-emulsifier permits formation of the small-volume average droplets of our invention (100 to 400 nm). In the absence of fatty acid emulsifier, the volume average of the droplets of petrolatum (using either isethionate or taurate surfactants as emulsifier) is well above 400 nanometers.

A further advantage of using fatty acid as co-emulsifier is that a more economical grade of sulfoalkyl ester and/or amide of fatty acids can be used to further reduce the cost of nanoemulsions. sulfoalkyl ester and amide of fatty acids are commercially made by reacting fatty acid (e.g., $C_{10}$ to $C_{18}$ fatty acid) with, for example, sodium isethionates ($HOCH^2CH^2SO_3^-Na^+$) and sodium methyltaurine ($NH^2CH^2CH^2SO_3^-Na^+$) respectively. In order for a high yield, fatty acid is typically in excess to boost the yield and reduce the side reactions (Anionic Surfactants Part 2, Surfactant Science Series, Vol. 7, p 458-461). At the end, the fatty acid is removed by vacuum distillation, which increases the cycle time and consumption of energy, and thus increases production cost. The undistilled mixture can very well be used to efficiently prepare pumpable nanoemulsion of desired oil droplets.

Specifically, the co-emulsifier (subject of the invention), allows preparation of particularly smaller petrolatum droplets (e.g., 300 nm and below, preferably 250 nm and below, more preferably 200 nm and below) in an efficient manner and further permits use of poorly soluble anionic mild surfactants in preparation of pumpable nanoemulsions at ambient temperature Skin moisturizing oils (including triglyceride oils and petrolatum benefit agents noted above) are often delivered from personal cleansing compositions (e.g., shower gels, facial and hand cleansers designed to cleanse and moisturize skin) in the form of large oil drops (e.g., 50 to 200 microns or greater).

U.S. Pat. Nos. 5,584,293 and 6,066,608, both to Glenn, Jr., for example, disclose a moisturizing liquid personal cleansing emulsion with at least 10% lipophilic skin moisturizing agent droplets having a diameter of greater than 200 microns.

U.S. Pat. No. 8,772,212 to Restrepo et al. discloses an isotropic cleansing composition containing high level of petrolatum; greater than 50% by volume of the petrolatum particles have a diameter greater than 50, 100, 150 or 200 microns.

Compositions containing large oil drops need to be well structured so they can suspend the large droplets (using, for example, stabilizers). U.S. Pat. Nos. 5,854,293 and 6,066,608, for example, utilize stabilizers selected from crystalline, hydroxyl-containing stabilizers, polymeric thickeners, $C_{10}$-$C_{18}$ diesters, amorphous silica or smectite clay.

Special blending processes are typically needed to prepare such compositions. For example, compositions must be prepared under low shear to prevent oil droplet size reduction (see U.S. Pat. No. 8,772,212). Although they provide enhanced delivery of benefit agents, these products are generally considered to be less aesthetically appealing to the consumer due to the presence of large oil droplets.

Another method of enhancing the delivery of a benefit agent (e.g., silicone) to the skin, for example, is through the use of cationic hydrophilic polymers such as, for example, hydroxypropyltrimethylammonium derivative of guar gum, sold under the name JAGUAR® C-13-S (see U.S. Pat. No. 5,500,152 to Helliwell). In this reference, silicone oil is a preformed emulsion with oil droplet size ranging from 0.1-1 micron (μm), with a mean particle size of 0.4 μm (there is no mention whether this refers to number average or volume average diameter of droplets). This kind of product tends to be smooth and aesthetically appealing. However, nourishing vegetable oils (triglyceride oils) and highly occlusive skin protectants, such as petrolatum, are typically preferred moisturizers from a cleansing composition.

One challenge facing cleansing compositions that are rich in moisturizing oils is that large amount of oils tend to depress the lather speed and volume.

It is therefore desirable to prepare a personal cleansing composition consisting of triglyceride oils and/or petrolatum nanoemulsion, which is aesthetically appealing, high in deposition of these moisturizing oils, and which maintains high lather performance.

In the subject invention, applicants provide novel o/w nanoemulsions for delivery of triglyceride oils and petrolatum as small (100 to 400 nanometers, particularly 120 to 300, more particularly 150 to 250) volume average diameter droplets. Further, unexpectedly, high lather performance is maintained.

As noted above, in co-pending applications, applicants claim o/w nanoemulsions comprising the salts of N-acyl derivatives of mono- or di-carboxylic amino acid, which can be supplied in the format of liquid solution with concentration ranging from 20 to 35% at ambient temperature. In this application, using fatty acids as co-emulsifiers, unexpectedly applicants have found they can create pumpable nanoemulsions at ambient temperature using poorly soluble anionic mild surfactants. Sulfoalkyl ester and amide of fatty acids are well known mild anionic surfactant with widespread applications in cosmetic compositions. They are less expensive compared with amino acid based surfactants in the previous applications.

Nanoemulsion of the invention comprise (1) an oil phase containing benefit agent droplets selected from the group consisting of triglyceride oils, petrolatum and mixtures thereof; and $C_8$ to $C_{18}$ fatty acid co-emulsifier and (2) an aqueous phase comprising one or more surfactants (primary emulsifier) which are sulfoalkyl ester of fatty acid or sulfoalkyl amide of fatty acids or mixtures of such.

The specific sulfoalkyl ester of fatty acid or sulfoalkyl amide of fatty acids typically comprise 70% or greater, preferably 75% or greater, more preferably 80% or greater of all surfactants present in the aqueous phase of the nanoemulson composition. Sulfoalkyl ester of fatty acid or sulfoalkyl amide of fatty acids are present in an amount greater than any other surfactant present in the aqueous phase. Additional ionic surfactants that help increase the solubility of sodium acyl isethionate or sodium methyl acyl taurate may be present in the aqueous phase. Such surfactants, termed as solubilizers, typically consist of head groups that are similar to or larger and more complicated than those of sodium acyl isethionate or sodium methyl acyl taurate. Anionic surfactants and amphoteric surfactants can serve this purpose. In the anionic surfactant category, these are (but not limited to): sodium (or ammonium) dialkyl sulfosuccinates, disodium (or diammonium) alkyl sulfosuccinates, disodium (or diammonium) alkyl ether sulfosuccinate, disodium (or diammonium) acyl glutamates, sodium (or ammonium) acyl lactylates, and sodium acyl sarcosinate. Sodium methyl acyl taurate and sodium acyl isethionate share the similar head group and thus help solubilize each other. In the amphoteric category, there are alkylamidopropyl hydroxysultaines, sodium (or ammonium) alkylamphoacetates, disodium (or diammonium) alkylamphodiacetates, sodium (or ammonium) alkylamphopropionates, disodium (or diammonium) alkyliminodipropionates, alkylamidopropylbetaines, and sodium alkylamphohydroxypropylsulfonate. The solubilizer surfactant typically comprises 30% or less, preferably 25% or less, more preferably 20% or less of all surfactants present in the aqueous phase of the nanoemulson composition.

In U.S. Pat. No. 6,541,018 to Simonnet et al, the internal phase oils are primarily lower molecular weight ester oils (MW less than 400). The lower MW ester oil impacts viscosity and lather of cleansing compositions. The triglycerides of our invention and the petrolatum (having melting point from 30° to 60° C.) of our invention help maintain good viscosity and foam.

It is noted that nanoemulsions disclosed in both U.S. Pat. Nos. 8,834,903 and 6,541,018 to Simonnet et al have an internal phase where concentration of oil is no higher than 40% of the emulsion. While the concentration of oils of the subject invention may range from 40% to 75% by wt. of total nanoemulsion, preferred ranges are 41 to 70%, preferably 50% to 65%. The higher internal phase is beneficial not only because it consumes less energy to prepare nanoemulsions of smaller droplets, but it also improves the yield of nano oil droplets.

US2003/0012759 A1 to Bowen-Leaver teaches preparation of nanoemulsion using high pressure devices at about 10,000 to 20,000 psi and with multiple passes ([0021] on page 3). It discloses an emulsifier system consisting of anionic surfactant (sodium stearoyl glutamate), non-ionic surfactants (glyceryl stearate/PEG-100 stearate) and stearic acid in Example 1. Fatty acid is used with glyceryl stearate/PEG-100 stearate as co-emulsifiers in oil phase. There is no mention of criticality of combining anionic surfactants, such as sodium acyl isethionate or sodium methyl acyl taurate, and fatty acid as emulsifiers to improve production efficiency of nanoemulsion and ambient temperature pumpability. In our application, non-ionic emulsifiers, such as glyceryl stearate and PEG-100 stearate, are not included in the emulsifier system for preparing nanoemulsions. The combination of anionic surfactants and fatty acid has been found to unexpectedly reduce petrolatum nanoemulsion droplet size to below 400 nm after only one pass and at 5,000 psi or less, without any other non-ionic surfactants present. Such process efficiency, based on use of fatty acid, is completely unpredictable.

WO 02/080864 A1 discloses oil-in-water nanoemulsions comprising as its principle emulsifiers a ternary system of surfactants comprising a cationic, anionic and bridging surfactant (lines 16-17, page 2). The nanoemulsion is prepared via a high pressure microfluidizer at 10,000 to 20,000 psi with at least two passes (lines 14-17, page 3)). Taurates and isethionates are two of the preferred anionic surfactants (claim 4) and fatty acid is optionally included in the surfactant blend of six surfactants in example 2 (lines 20~21). No mention is made of specific advantages due to addition of fatty acid. The oil level in the nanoemulsion is less than 30% while the oil level in our application is 40% and above.

US2003/0077299 A1 discloses an o/w nanoemulsion comprising an ionic surfactant, a water phase and an oil phase which either comprises a ceramide or fatty acid. N-methyl-N-myristoyl taurate and sodium N-stearoyl-N-methyl taurate are two of many examples of anionic surfactants (lines 6~8 in [0016] on page 1). In Example 1 emulsion (3), nanoemulsion containing 16.4% silicone oil and 5% ceramide is prepared at a pressure of 2,800 kg/cm2 (about 40,000 psi) with three passes ([0060] on page 4), using sodium N-stearoyl-N-methyl taurate as emulsifier. The oil level is far below 40 to 75%. No fatty acid is used to reduce the processing energy in preparing nanoemulsions, especially when petroleum Jelly is concerned.

US20090062406A discloses aqueous surfactant concentrates consisting of isethionate, taurate and betaine surfactants, which is flowable and transparent. However, no nano oil droplets are present.

A previously mentioned U.S. Pat. No. 5,500,152 to Helliwell discloses in Example 1 a shower gel containing surfactants mixture (9% sodium cocoyl isethionate and 6% coconut betaine) and 5% silicones oil with a mean particles size of 0.4 μm (400 nm). The silicone oil was added as a preformed emulsion containing 50% silicone oil, 2% laury alcohol ethoxylate 2EO and 2% laury alcohol ethoxylate 21EO. No mention was made of sodium cocoyl isethionate and fatty acid being used as emulsifier to form nanoemulsion so to create an ethoxylates free cleansing composition as it is the case of our application.

US Publication 2017/0087064 to Ikeda et (L'Oreal) relate to compositions which may either be in the form of nano or microemulsion; or which may be lamellar structured (paragraph 0001). Example 4 (Table 5, page 23) discloses a formulation that has a Polyglycerol-5 Oleate and Polyglerol-2 Caprate (nonionic emulsifiers used as primary surfactant), as well as minor amounts (0.2%) of sodium methyl stearoyl taurate to form a lamellar structure. There is no mention of formation of oil droplets having a size less than 300 nanometers; and no suggestion of formation of a nanoemulsion such as is clearly noted in, for example, Examples 1 and 2.

The unique nanoemulsions of the present invention contain small oil droplets (400 nanometers or less) which are aesthetically pleasing, efficiently deliver the benefit agent triglycerides oils or petrolatum, and maintain excellent lather when being incorporated into personal cleansing compositions. Further, the specific surfactants used, provide excellent, "mild" cleansing and ensure foam maintenance when the nanoemulsons are used in personal cleansing products.

BRIEF DESCRIPTION OF THE INVENTION

Specifically, the present invention relates to a nanoemulsion compositions comprising:

a) an internal oil phase comprising (i) 40 to 75% by wt. of total nanoemulsion of oil selected from the group consisting of triglyceride oil, petrolatum and mixtures thereof, wherein the melting point of the petrolatum is 30 to 60° C.; and (ii) 0.8 to 10% by wt. nanoemulsion of a $C_8$ to $C_{18}$, preferably $C_{10}$ to $C_{14}$ fatty acid (e.g., $C_{12}$ lauric acid), and b) an external aqueous phase comprising 1.6 to 10% by wt. (as active) of total nanoemulsion of sulfoalkyl ester of fatty acid or sulfoalkyl amide of fatty acids, or mixture of two
wherein the surfactant of (b) comprises 70% or greater of all surfactant present in aqueous phase of the nanoemulsion.
wherein the volume average diameter of the oil droplets of (a) is 100 to 400 nanometers,
wherein the nanoemulsion is pumpable at ambient temperature.

Preferably sulfoalkyl ester of fatty acid is an alkali metal or ammonium salt of acyl isethionate. Preferred molecules include sodium or potassium acyl isethionate, preferably sodium acyl isethionate. Preferably, sulfoalkyl amide of fatty acids is an alkali metal (especially sodium or potassium) short chain (c1 to c3) alkyl, alkyl taurate. A preferred molecule is alkali metal methyl, alkyl taurate and especially preferred is sodium methyl alkyl taurate. Sodium cocoyl isethionate and sodium methyl alkyl taurate has a solubility of only 0.01% and 1% by weight in water at 25 C respectively.

Preferably, compositions of the invention comprise, in addition to fatty acid in oil phase, additional surfactant solubilizer (at levels of less than 30% of all surfactants in aqueous phase); preferably the additional surfactant is anionic or amphoteric surfactant or mixtures of both.

It should be understood that the claims are directed to the composition. That is, the claim is intended to cover sulfoalkyl ester of fatty acids and sulfoalkyl amide of fatty acids, for example, whether formed by us or bought as a prepared surfactant product (as would occur in the vast majority of all cases).

Using fatty acid as co-emulsifier, nanoemulsions of the invention will typically have volume average diameter of droplets of 400 or less, or 100 to 350; or 120 to 300; or 150 to 250. Due to use of fatty acid as co-emulsifier, nanoemulsion based on poorly soluble surfactants, especially sodium acyl isethionate, do not solidify and are pumpable at ambient temperature.

The nanoemulsions are typically prepared by mixing the oil phase and the aqueous phase using a conventional rotor/stator or other type of high shear devices and further processed via homogenizer at a process pressure of 5000 pounds per square inch (psi) or less, preferably 4500 psi or less. Using the same components, but no $C_8$ to $C_{18}$ fatty acid as co-emulsifier in the oil phase, at the same pressure the droplet size will be typically much higher than if fatty acid is used.

Because sulfoalkyl ester of fatty acids, for example, sodium acyl isethionate, and sulfoalkyl amide of fatty acids, for example, sodium methyl alkyl taurates are mild cleansing surfactants, and are sulphate and ethoxylate free, the nanoemulsion composition, once formed, provides several advantages. For example, the nanoemulsion composition can be readily incorporated into a wide range of personal cleanser compositions. Further, sodium acyl isethionate, and sodium methyl alkyl taurates, enable good lather formation of cleanser composition. Furthermore, when aided with cationic polymer, the subject nanoemulsion significantly improves oil deposition onto skin from cleansing compostions. Compared with the more expensive mono- or dicarboxylic amino acid based surfactants and nanoemulsion made with those surfactants, the subject nanoemulsions provide a route for more affordable mild and moisturizing cleansing compositions Thus, the novel nanoemulsions are sensorially pleasing (due to small droplet size), provide efficient oil deposition, provide superior stability (again because of smaller droplet size), and are ideally suited for use in personal cleansing compositions while being more cost effective.

In another aspect, the invention relates to process for preparing an emulsion comprising:
 a. an internal oil phase comprising (i) 40 to 75% by wt. of total nanoemulsion of oil selected from the group consisting of triglyceride oil, petrolatum and mixtures thereof, wherein the melting point of the petrolatum is 30 to 60° C.; and (ii) 0.8 to 10% by wt. nanoemulsion of a $C_8$ to $C_{18}$, preferably $C_{10}$ to $C_{14}$ fatty acid (e.g., $C_{12}$ lauric acid), and
 b. an external aqueous phase comprising 1.6 to 10% by wt. (as active) of total nanoemulsion of a surfactant or surfactants which are sulfoalkyl ester of fatty acid, e.g., sodium acyl isethionate, sulfoalkyl amide of fatty acid, e.g., sodium methyl alkyl taurates, or mixture of the two
 wherein the volume average diameter of the oil droplets of (a) is 100 to 400 nanometers.
 wherein the nanoemulsion is pumpable at ambient temperature
 wherein said process comprises:
  1) heating aqueous phase to 55 to 75° C.;
  2) heating oil phase to 55 to 75° C. or until molten;
  3) adding oil phase to aqueous phase under agitation and mixing further to form coarse emulsions with a rotor/stator high shear device at a speed of 1000 to 6000 revolution per minute (rpm);
  4) pumping the coarse emulsion once through homogenizer at process pressure of 5000 psi or less, preferably 4500 psi or less; and
  5) cooling nanoemulsion to ambient temperature.

In step 3), alternatively, the coarse emulsion may be formed using a homogenizer operating at pressure of 200 to 500 psi.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

The present invention provides novel nanoemulsions containing a specific selection of oils and surfactants. The nanoemulsions can be prepared using processing pressure of 5000 psi or less. The novel nanoemulsions are ideally suited for use in cleansing compositions, for example, liquid cleansing compositions or soap bars.

Specifically, sulfoalkyl ester of fatty acid, such as sodium acyl isethionate, or sulfoalkyl amide of fatty acid, such as sodium methyl alkyl taurates have greater than 65%, preferably greater than 75%, preferably greater than 80% of $C_{14}$ or less acyl or alkyl chain (preferably they have greater than 75% acyl or alkyl chain which are $C_{12}$, $C_{14}$ and mixtures thereof). The chosen emulsifiers provide multiple advantages when final nanoemulsions are mixed into fully formulated liquid personal cleansing compositions. First, the isethionate and taurate surfactants are known to be less irritating than harsher surfactants typically used such as sodium lauryl sulphate and sodium lauryl ether sulphate (SLES). Also, as noted, the chain length is selected so the surfactants are suitable for use in personal cleansing compositions while providing minimal interference with such product structuring. Further, the selected predominantly shorter chain lengths ensure the surfactants will provide good foam.

In a co-pending application, applicants claim similar nanoemulsions which comprise N-acyl derivatives of di-carboxylic amino acids and which are more expensive and can be supplied in the format of liquid solution with 20 to 35% actives. Small size oil droplets are obtained with fatty acid being used as co-emulsifier.

In this application, poorly soluble anionic surfactants, e.g. sodium acyl isethionate, when used as emulsifier, tend to yield oil droplets that are larger, e.g., greater than 400 nanometer (nm) after one pass through a high pressure homogenizer at 5000 pounds per square inch (psi) pressure. Further, nanoemulsions made with sodium acyl isethionate tend to solidify at ambient temperature and are thus difficult to pump. Unexpectedly we have found that using fatty acid as co-emulsifier yields significantly smaller droplets, and these small droplet nanoemulsions are obtained more efficiently. Surprisingly, even when no solubilizer of sodium acyl isethionate is used, the subject nanoemulsion is pumpable at ambient temperature. Use of a solubilizer, however, further enhances the pumpability of nanoemulsion. Small droplet size and efficient processing is function of specific combination of specific surfactants (e.g., anionic) and specifically fatty acid. That is, a unique synergy between surfactants of the invention and fatty acid, as noted, works particularly well with oils (e.g. petroleum jelly) of the invention.

In short, significantly smaller droplets are obtained (using fatty acids) when using the same materials, and these small droplet nanoemulsions are obtained more efficiently and are pumpable at ambient temperature. In general, small volume average size droplets help provide more efficient deposition. For example, cationic polymers typically used in fully formulated liquid cleanser more readily deposit the smaller droplets than larger droplets. Large oil droplets also require stabilizers to suspend the large oil droplets. The small size oil droplets from the nanoemulsion, when incorporated into a cleansing liquid, also provide greater stability. Small droplets are also viewed as more aesthetically pleasing.

The nanoemulsions of the invention are defined with more particularity below.

Oil Phase

Oils in the oil phase of the nanoemulsions may be triglyceride oil or oils (animal and/or vegetable oils); petrolatum; or mixtures of one or more triglyceride oil with petrolatum. Petrolatum is particularly preferred.

Examples of triglyceride oils which may be used include soybean oil, sunflower seed oil, coconut oil, rapeseed oil, palm oil, palm kernel oil, grape seed oil, shea butter, cocoa butter and fish oil. Soybean and sunflower seed oils are preferred triglycerides.

The oil in the oil phase may also be petrolatum. The petrolatum preferably has a melting point ranging from 30° to about 60° C. Examples of such petrolatum oils include Vaseline® Petroleum Jelly from Unilever, White Petrolatum USP from Calumet Penreco, Petrolatum G2212 and White Protopet® 1S from Sonneborn.

Also suitable are the vegetable oils gelled with beeswax or vegetable wax. Examples of such gelled vegetable oils include NaturalAtum from Koster Keunen, Inc. and Unpetroleum Jelly from Camden-Grey Essential Oils, Inc.

The oils range from 40% to 75% by wt., preferably 41% to 65% by wt. of the total nanoemulsion composition. The preferred volume average diameter of the triglyceride oil or petrolatum droplets is 100 to 400 nm, preferably 120 to 350 nm, more preferably 150 to 300 nm.

The choice of triglyceride oils and petrolatum helps impart emolliency and occlusivity to skin when the triglyceride oils and/or petrolatum deposit onto skin after the skin is washed with fully formulated cleansing compositions into which the nanoemulsions of this invention have been incorporated.

In addition to the triglyceride oil (or oils) and/or petrolatum, the oil phase may comprise oil soluble skin beneficial actives such as, for example, Vitamin A, Vitamin E, sun screen, fragrances, retinol palmitate, 12-hydroxy stearic acid, conjugated linoleic acid; antibaterial agents; mosquito repellents etc. at level of 0.01 to 5%.

Another ingredient which might be found in the oil phase is an oil phase stabilizer. For example, small amounts (0.01 to 2%, preferably 0.1-1% by wt. nanoemulsion) of antioxidant may be used. When the oil used is triglyceride, a preferred antioxidant which may be used is butylated hydroxytoluene (BHT). This is often used as a food grade antioxidant.

In addition to oils, the oil phase contains $C_8$ to $C_{20}$, preferably $C_{10}$ to $C_{14}$ fatty acids in an amount ranging from 0.8 to 10%, preferably 1 to 7% by wt. total nanoemulsion.

Examples of fatty acid which may be used include lauric acid, myristic acid, palmitic acid, stearic acid, coconut fatty acid and mixtures thereof. Preferably, lauric acid is used as a co-emulsifier. For example, the oil phase may contain petrolatum ranging from 40 to 70% by wt, preferably 41 to 65% by wt. of nanoemulsion and lauric acid ranging from 0.9 to 8% by wt. of nanoemulsion.

Aqueous Phase

The aqueous phase contain poorly water soluble anionic surfactants, sodium acyl isethionate, or sodium methyl alkyl taurates or both. The solubility of these surfactants ranges from 0.01 to 1% at ambient temperature. These surfactants have greater than 65%, preferably greater than 75%, preferably greater than 80% of $C_{14}$ or less acyl or alkyl chain (preferably they have greater than 75% acyl or alkyl chain which are $C_{12}$, $C_{14}$ and mixtures thereof). Preferred acyl isethionate is cocoyl or lauryl isethionate and preferred taurates are cocoyl or lauryl taurate. These predominantly short chain acyl groups (relative to longer chain C16 and C18, for example) ensure that, when nanoemulsions of the invention are incorporated into fully formulated cleansing compositions (e.g. liquid cleansing compositions), they help maintain or enhance foaming capacity.

The acyl isethionate surfactant component is typically prepared by the reaction of an isethionates salt and an fatty acid having 8 to 20 carbon atoms and Iodine Value (measuring degree of unsaturation) of less than 20, for example:

$$HOR^1SO_3M + RCOOH \rightarrow RCOOR^1SO_3M$$

where $R^1$ is an aliphatic hydrocarbon radical containing 2 to 4 carbons;

M is alkali metal cation (e.g., sodium, potassium), ammonium or substituted ammonium cation or other counterion; and R is an aliphatic hydrocarbon radical having 7 to 21, preferably 9 to 17 carbons.

Depending on the processing conditions used, the resulting fatty acyl isethionate product can be a mixture of 40 to 85% by weight of fatty acyl isethionates (which formed from the reaction) and 50 to about 12 wt. %, typically 40 to 20 wt. % of free fatty acids. In addition, product may contain isethionates salts which are present typically at levels less than 5 wt. %, and traces (less than 2 wt. %) of other impurities. The acyl chain length distribution of fatty acyl isethionate is controlled by the chain length distribution of fatty acids. Preferably, a mixture of fatty acids is used for the preparation of commercial acyl isethionates surfactants. Typically coconut fatty acid is used, which is rich in lauric acid, resulting in cocoyl isethionate. The chain length distribution can be further adjusted by blending different cuts of distilled fatty acids to enrich a certain chain length, e.g., $C_{12}$, in the final reaction product. The resulting acyl isethionate surfactants (e.g., resulting from reaction of alkali metal isethionate and aliphatic fatty acid) should have more than 65 wt. %, preferably more than 75%, (on basis of acyl isethionates reaction product) of acyl group with 14 or less carbon atoms to provide both lather and mildness of the resulting acyl isethionate product. The resulting acyl isethionate surfactants and unreacted fatty acids, form poorly soluble surfactant/fatty acid crystals typically in water at ambient temperatures.

Examples of commercial acyl isethionate products that are particularly useful in the subject invention are DEFI flakes, a main ingredient in Dove® bar soap produced by Unilever. DEFI (Direct Esterification of Fatty Isethionate) flakes typically contain about 68 to 85 wt. % of sodium fatty acyl isethionate and 12 to 30 wt. % free fatty acid. More than 65 wt. % and preferably more than 75% of acyl group of the resulting acyl isethionate have 14 or less carbon atoms. The acyl isethionate surfactant products are extremely mild to skin and have very good lather.

Other suppliers of acyl isethionate include Huanggang Yongan (e.g. YA-SCI-65 and YA-SCI-85), Innospec (e.g. Pureact SLI), Clariant (e.g. Hostapon® SCI-85 P).

Sodium methyl alkyl taurates are closely related to acyl isethionate structurally and synthetically. The precursor of sodium methyl alkyl taurates, N-methyltaurine, can be prepared from sodium isethionate economically:

$$H_2NCH_3 + HOCH_2CH_2SO_3M \rightarrow HN(CH_3)CH_2CH_2SO_3Na + H_2O$$

where M is alkali metal cation (e.g. sodium, potassium), ammonium or substituted ammonium or other countries.

N-methyltaurine, for example, further reacts with fatty acid, resulting sodium methyl alkyl taurates:

$$HN(CH_3)CH_2CH_2SO_3Na + RCOOH \rightarrow RCON(CH_3)CH_2CH_2SO_3Na$$

R is an aliphatic hydrocarbon radical having 7 to 21, preferably 9 to 17 carbons.

As with the acyl isethionate, the resulting alkyl taurate product, e.g., sodium methyl alkyl taurates, can be a mixture sodium methyl alkyl taurates, free fatty acid and other residues. The chain length distribution of fatty acids used dictates the chain length distribution of alkyl taurates. Typically coconut fatty acid is used, which is rich in lauric acid, resulting cocoyl taurates. The chain length distribution can be further adjusted by blending different cuts of distilled fatty acids to enrich a certain chain length, e.g., 12 carbons, in the final reaction product. The resulting fatty alkyl taurate surfactants should have more than 65 wt. %, preferably more than 75%, (on basis of alkyl taurate reaction product) of fatty acyl group with 14 or less carbon atoms to provide both lather and mildness of the resulting fatty alkyl taurate product. The solubility of sodium methyl cocoyl taurate in water is around 1% by weight at 25 C. It can be supplied as a paste with 20~35% active, e.g. Pureact WS Conc., a 30% active material, from Innospec. Other suppliers include Galaxy (e.g. Galsoft SLT), Solvay Novecare (Geropon® TC-42 LQ), Croda (Adinol CT95) and Clariant (Hostapon CT Paste)

When sodium cocoyl isethionate and sodium methyl cocoyl taurate are used to prepare petrolatum nanoemulsion as sole emulsifier using homogenizer at 5000 psi, both yield oil droplets well above 400 nm; moreover, the sodium cocoyl isethionate based emulsion solidifies at ambient temperature upon storage, making it unpumpable. This is due to the limited solubility of sodium acyl isethionate in water, causing it to crystalize in the aqueous phase of emulsion and making the emulsion unpumpable. The conventional way to solve the pumpability issue is to use solubilizers of sodium cocoyl isethionate in aqueous phase to help dissolve it. Such solubilizers are ionic surfactants consisting of head groups that are similar to or larger and more complicated than those of sodium acyl isethionate. Both anionic and amphoteric surfactants can serve this purpose. A major unexpected discovery of this invention is that, instead of using solubilizers, using fatty acid as co-emulsifier not only prevents the emulsion based on sodium acyl isethionate from solidifying, and thus be pumpable, but also significantly reduces the size of oil droplets to half or a third of those when no fatty acid is used. The addition of a fatty acid, especially lauric acid, as a co-emulsifier results in the formation of pumpable nanoemulsion and the efficient formation of smaller oil droplets to form a highly superior nanoemulsion. For example, it was possible to produce petrolatum oil droplet sizes around 200 nm with only one pass through the homogenizer at 5000 psi (see Example 1).

Additionally, other mild ionic cleansing surfactants, which also serves as solubilizers, can be used in the aqueous phase. Anionic surfactants which may be used include amino acid based surfactants, such as acylglutamate, acylaspartate, acylglycinate, acylalaninate and acyl sarcosinate. Amphoterics such as coco betaine, cocamidopropyl betaine, sodium lauroamphoacetate, Lauramidopropyl hydroxysultaine and Cocamidopropyl hydroxysultaine can also be used and are preferred. These co-surfactants are typically present at a level of less than 30% of total surfactants in the aqueous phase. Non-ionic surfactants should preferably be avoided in the aqueous phase as those surfactants typically yields poor lather.

Overall surfactants in aqueous phase comprise 1.6 to 10% preferably 4 to 8% by wt. of total nanoemulsion. As indicated the poorly soluble sodium acyl isethionate, or sodium methyl acyl taurate or mixtures thereof are the principal surfactant of the nanoemulsion. They constitute 70% or greater, preferably 80% or greater of all surfactant in the aqueous phase. They may of course be the only surfactant present in the aqueous phase.

Preferably, the aqueous phase may contain a preservative or preservatives. Typically, they are present at a level of 0.01 to 1.0%, preferably 0.1 to 0.5% by wt.

Additionally, polyols may be included in the aqueous phase. Examples of polyol are glycerol, sorbitol, hydroxypropyl sorbitol, hexyleneglycol, 1,3-butylene glycol, 1,2,6-hexanetriol, ethoxylated glycerine, propoxylated glycerine or mixtures thereof. When water soluble alkali metal (e.g. Potassium) or ammonium salt of acyl isethionate and/or alkyl taurate is used as primary anionic emulsifier, the level of polyol in the aqueous phase may be significantly high, resulting in a polyol to water weight ratio from 1:3 to 3:1. This ratio may improve the production efficiency of nanoemulsion, eliminating the need of high pressure homogenization. Minimal or no polyols (e.g. 0 to 5%, preferably 3% or less or 2% by wt or less) should be included in the aqueous phase when sodium salt of acyl isethionate and/or alkyl taurate is used as the primary anionic emulsifier due to their poor solubility in water.

Nanoemulsions of the invention, have volume average diameter (also used interchangeably in and with terms "volume mean diameter" or "volume average size") of 400 nm or less, preferably 100 nm to 350 nm, more preferably 120 to 300 nm.

Nanoemulsions with droplet sizes of these ranges are obtained in the subject invention using a high pressure homogenizer or a high pressure sonolator. Pressures used are 5000 psi or less, preferably 4500 psi or less.

Preparation of Nanoemulsion

Nanoemulsions are typically formed in a two-stage process.

The first stage is used to form a coarse emulsion. The oil phase and aqueous phase were heated up to 75° C. (55° to 75° C.) separately such that each phase was clear and uniform (oil phase heated to 55 to 75° C. or until molten); then the oil phase was mixed with the aqueous phase with intensive mixing. Intensive mixing can be accomplished via conventional means including mixing the materials in a stirred tank and passing the mixture through a rotor/stator mixer such as the Silverson® high shear in-line mixer or mixing them in the vessel with a high shear mixer such as the Scott® Turbon mixer. Alternatively, the coarse emulsion may be created by using a continuous high shear mixing device such as the standard Sonolator device produced by Sonic Corporation of Connecticut. These standard sonolators are normally operated at pressures of 200-500 psi to form coarse emulsion.

The second stage of the process is to pass the coarse emulsion through a high pressure homogenizer to form the nanoemulsion. High pressure homogenizers used in this invention are the Nano DeBee homogenizer of BEE International (Massachusetts, USA) and the High Pressure Sonolator device also produced by Sonic Corporation of Connecticut, USA. These devices can be operated up to 1000-5000 psi in order to produce nanoemulsions of less than 400 nm. The homogenizers from other suppliers can be used as long as it can be operated up to 1000-5000 psi. For hydrophobic oils, either petrolatum or triglycerides, only one pass through the Nano DeBEE or high pressure sonolator is required to reach the desired nano-emulsion particle size, when fatty acid is included as co-emulsifier.

In the examples, the following terms are defined as noted below:

D[4, 3]: volume average diameter or volume mean diameter or volume average size

The volume average diameters are determined by a Malvern Mastersizer.

Examples 1-4 and Comparatives A

Coarse emulsions were prepared in a one liter ESCO mixer equipped with a rotor/stator high shear device (ESCO-LABOR AG, Switzerland). The aqueous phase was added to the ESCO mixer and heated up to 75° C. or till clear. The oil phase was combined and heated up to 75° C. or till molten in a separate container. The oil phase was gradually added to the aqueous phase in the ESCO mixer under agitation and/or was intensively mixed by the rotor/stator device. When the addition of all oil phase was completed and the coarse emulsion was formed in the ESCO mixer, the coarse emulsion was transferred and passed through High Pressure homogenizer Nano DeBEE one time to arrive at the desired droplet size at a process pressure of 5000 psi.

| Ingredient | Comp. A Wt. % | Example 1 Wt % | Example 2 Wt % | Example 3 Wt % | Example 4 Wt % |
|---|---|---|---|---|---|
| Oil Phase | | | | | |
| Petrolatum G2212 | 55 | 55 | 55 | 55 | 55 |
| Lauric acid | | 3.5 | 3.5 | 4 | 4 |
| Aqueous phase | | | | | |
| Sodium cocoyl isethionate (YA-SCI-85)* | 6.0 | 6.0 | 6.0 | 5 | 4.5 |
| Na Methyl Cocoyl Taurate(Pureact WS-70, 20%) | | | | | 7.5 (1.5 active) |
| Na Methyl Cocoyl Taurate(Pureact WS CONC, 30%) | | | | 3.33 (1 active) | |
| Na Lauroamphoacetate (30%) | | | 6.67 (2 active) | | |
| Deionized Water | Q.S.** | Q.S.** | Q.S.** | Q.S.** | Q.S.** |
| Presevative | <1 | <1 | <1 | <1 | <1 |
| $D_{[4, 3]}$ nm | 425 | 215 | 191 | 231 | 234 |
| pH | 6.44 | 5.10 | 6.69 | 5.39 | 5.81 |
| Pumability at ambient temperature | Solid not pumpable | Cream Pumpable | Lotion Pumpable | Lotion Pumpable | Lotion pumpable |

*YA-SCI-85 contains 84% Sodium cocoyl isethionate, 12% fatty acid and 4% sodium isethionate
**Amount needed (e.g., to obtain 100% by wt.)

In Comparatives A, sodium cocoyl isethionate is the only emulsifier for preparation of nanoemulsion of petrolatum. The oil droplet size is 425 nm, above 400 nm. Most undersirably, the emulsion produced solidifies to the shape of its container when at ambient temperature upon storage due to the limited solubility of sodium cocoyl isethionate. The emulsion made in Comparison A cannot be pumped at ambient temperature due to its solid nature. In Example 1, when 3.5% fatty acid (not a solubilizer of sodium cocoyl isethionate) is used as co-emulsifier, the oil droplet size is reduced by half to 215 nm and, most unexpectedly, the nanoemulsion produced has a skin cream consistency and can be readily pumped at ambient temperature upon storage. In Examples 2~4, both fatty acid and solubilizers of sodium cocoyl isethionate, such as Na Lauroamphoacetate and Na Methyl Cocoyl Taurate, are incorporated into the emulsion formula, resulting nanoemulsion of droplet size ranging 191~234 nm, and the lotion like emulsions that are readily pumpable at ambient temperature upon storage.

Examples 5~6 and Comparatives B~C

Examples 5~6 and comparatives B~C were prepared similarly to Examples 1-4 and Comparatives A.

| Ingredient | Comp. B Wt % | Example 5 Wt % | Comp. C Wt % | Example 6 Wt % |
|---|---|---|---|---|
| Oil Phase | | | | |
| Petrolatum G2212 | 55 | 55 | 51.56 | 51.56 |
| Lauric acid | | 4 | | 3.75 |

-continued

| Ingredient | Comp. B Wt % | Example 5 Wt % | Comp. C Wt % | Example 6 Wt % |
|---|---|---|---|---|
| Aqueous Phase | | | | |
| Na Methyl Cocoyl Taurate(Pureact WS-70, 20% Active) | 30 (6 active) | 30 (6 active) | 28.13 (5.6 active) | 28.13 (5.6 active) |
| Na Lauroamphoacetate (30%) | | | 6.25 (1.88) | 6.25 (1.88) |
| Deionized Water | Q.S.* | Q.S.* | Q.S.* | Q.S.* |
| Preservatives | <1 | <1 | <1 | <1 |
| $D_{[4, 3]}$ nm | 606 | 262 | 469 | 213 |
| pH | 9.30 | 6.2 | 9.43 | 6.67 |
| Pumability at ambient temperature | Pumpable | Pumpable | Pumpable | Pumpable |

*Amount needed (e.g., to obtain 100% by wt.)

In comparative B, Na Methyl Cocoyl Taurate is supplied as a 20% dispersion. Due to its low solubility, the dispersion is white paste. When used as the only emulsifier, the resulting emulsion produced after being processed via homogenization at 5000 psi, yields oil droplet of 600 nm, even far greater than that in Comparative A, where sodium cocoyl isethionate is used, though the former is pumpable and latter not pumpable, possibly due to their difference in solubility in water at ambient temperature. In Example 5, with fatty acid as co-emulsifier, the oil droplet size is reduced more than half to 262 nm in the resulting nanoemulsion.

Examples 7-10

60% Petrolatum was used to form nanoemulsions, with sodium cocoyl isethionate (YA-SCI-85) as primary emulsifier in aqueous phase and lauric acid as co-emulsifier in oil phase. The coarse emulsion was prepared in a 450 lbs stirred jacketed tank, equipped with an off-center turbine, a scraper and a recirculation loop along which a pump and a Silverson in-line rotor/stator double screen mixer (Model 150/250 MS) were attached. The aqueous phase was added to the tank and heated up to 75 C, while the oil phase was heated up to 75 C in a separate tank. The oil phase was then charged into aqueous phase via the recirculation loop with the in-line rotor/stator double screen mixer running at 6000 rpm while the pump was pumping the aqueous phase through the recirculation loop. After the completion of addition of oil phase, the mixture in the stirred tank was pumped through the recirculation loop 3 theoretical passes (=volume of mixture in tank divided by the flow rate in recirculation loop) with the in-line rotor/stator double screen mixer running at 6000 rpm. The coarse emulsion was then pumped through a high pressure sonolator only once with a pressure up to 2500 psi to form nanoemulsions.

| Ingredient | Example 7 | Example 8 Wt % | Example 9 | Example 10 |
|---|---|---|---|---|
| Oil Phase | | | | |
| Petrolatum G2212 | | 60 | | |
| Lauric acid | | 3.8 | | |
| Aqueous phase | | | | |
| Sodium cocoyl isethionate (YA-SCI-85)* | | 6.0 | | |
| Deionized Water | | Q.S.** | | |
| Preservative | | <1 | | |
| Process pressure, PSI | 1000 | 1500 | 2000 | 2500 |
| $D_{[4, 3]}$ nm | 368 | 305 | 245 | 209 |
| pH | | 5.38 | | |
| Pumability at ambient temperature | | Pumpable | | |

*YA-SCI-85 contains 84% Sodium cocoyl isethionate, 12% fatty acid and 4% sodium isethionate
**Amount needed (e.g., to obtain 100% by wt.)

The invention claimed is:
1. A nanoemulsion composition comprising:
 a) an internal phase comprising
  (i) 40 to 75% by wt. of total nanoemulsion composition of oils selected from the group consisting of triglyceride, petrolatum and mixtures thereof, wherein the melting point of the petrolatum is 30 to 60° C.; and
  (ii) 0.8 to 10% by wt. nanoemulsion of a $C_8$ to $C_{18}$ fatty acid; and
 b) an external aqueous phase comprising 1.6 to 15% by wt. (as active) of total nanoemulsion composition of a surfactant or surfactants which are an alkali metal or ammonium salt of isethionate; alkali metal C1 to C3 alkyl, alkyl taurate; or mixture of the two,
wherein the surfactant or surfactants which are an alkali metal or ammonium salt of isethionate; alkali metal C1 to C3 alkyl, alkyl taurate; or mixture of the two comprises 70% or greater of all surfactants present in said external aqueous phase of the nanoemulsion;

wherein the volume average diameter of droplets of the internal phase is 100 to 400 nanometers.

2. The nanoemulsion composition according to claim 1, wherein said alkali metal or ammonium salt of isethionate is sodium acyl isethionate.

3. The nanoemulsion composition according to claim 1, wherein said alkali metal C1 to C3 alkyl and wherein said alkyl taurate is sodium methyl alkyl taurate.

4. The nanoemulsion composition according to claim 1, wherein volume average diameter is 120 to 300 nanometers.

5. The nanoemulsion composition according to claim 1 further comprising surfactant in the aqueous phase selected from the group consisting of cocobetaine, cocoamidopropyl betaine, lauroamphoacetate, hydroxysultaine and mixtures thereof.

6. The nanoemulsion composition according to claim 5, wherein said additional surfactant comprises up to 30% by wt. of aqueous phase surfactant.

7. The nanoemulsion composition according to claim 1, wherein the oil is a triglyceride oil and said triglyceride oil is selected from the group consisting of soybean oil, sunflower seed oil, coconut oil, rapeseed oil, palm oil, palm kernel oil, grape seed oil, fish oil and mixtures thereof.

8. The nanoemulsion composition according to claim 1, wherein the oil is petrolatum and the melting point of the petrolatum is 30 to 60° C.

9. The nanoemulsion composition according to claim 1, wherein the oil is an oil mixture comprising triglyceride oil and petrolatum.

10. The nanoemulsion composition according to claim 1, wherein said fatty acid having a chain length $C_8$-$C_{18}$ is selected from the group consisting of lauric acid, myristic acid, coconut fatty acid and mixtures thereof.

11. The nanoemulsion composition according to claim 10, wherein the fatty acid is present at a level of 1 to 7% by wt. of said nanoemulsion.

12. The nanoemulsion composition according to claim 1, wherein the nanoemulsion is prepared at pressure from a homogenizer or sonolator and said pressure is 5000 psi or below.

13. A process for preparing an emulsion comprising:
   a) an internal phase comprising
      (i) 40 to 75% by wt. of total nanoemulsion composition of oils selected from the group consisting of triglyceride, petrolatum and mixtures thereof, wherein the melting point of the petrolatum is 30 to 60° C.; and
      (ii) 0.8 to 10% by wt. nanoemulsion of a $C_8$ to $C_{18}$ fatty acid; and
   b) an external aqueous phase comprising 1.6 to 15% by wt. (as active) of total nanoemulsion composition of a surfactant or surfactants which are an alkali metal or ammonium salt of isethionate; alkali metal C1 to C3 alkyl, alkyl taurate; or mixture of the two
wherein the surfactant or surfactants which are an alkali metal or ammonium salt of isethionate; alkali metal C1 to C3 alkyl, alkyl taurate sulfoalkyl ester or amide of fatty acids, or mixture of the two comprises 70% or greater of all surfactants present in the aqueous phase of the nanoemulsion;
wherein the volume average diameter of the oil droplets of the internal phase is 100 to 400 nanometers
wherein said process comprises:
   1) heating aqueous phase to 55 to 75° C.;
   2) heating oil phase to 55 to 75° C. or until molten;
   3) adding oil phase to aqueous phase and mixing to form coarse emulsions using a rotor/stator high shear device at 1000 to 6000 revolutions per minute (rpm),
   4) pumping the coarse emulsion once through a homogenizer at process pressure of 5000 psi or less; and
   5) cooling emulsion to ambient temperature.

14. The process according to claim 13, wherein in step 3), alternatively, the coarse emulsion is formed using a homogenizer operating at pressure of 200 to 500 psi.

\* \* \* \* \*